(12) United States Patent
Gepstein et al.

(10) Patent No.: US 9,624,503 B2
(45) Date of Patent: Apr. 18, 2017

(54) DROUGHT-RESISTANT PLANTS

(75) Inventors: Shimon Gepstein, Haifa (IL); Amira Gepstein, Haifa (IL); Eduardo Blumwald, Davis, CA (US)

(73) Assignees: The Regents of the University of California, Oakland, CA (US); Technion Research and Development Coundation, Haifa (IL)

( * ) Notice: Subject to any disclaimer, the term of this patent is extended or adjusted under 35 U.S.C. 154(b) by 1299 days.

(21) Appl. No.: 11/909,262

(22) PCT Filed: Mar. 21, 2006

(86) PCT No.: PCT/US2006/010678
§ 371 (c)(1),
(2), (4) Date: May 12, 2008

(87) PCT Pub. No.: WO2006/102559
PCT Pub. Date: Sep. 28, 2006

(65) Prior Publication Data
US 2008/0282365 A1 Nov. 13, 2008

Related U.S. Application Data

(60) Provisional application No. 60/664,035, filed on Mar. 21, 2005.

(51) Int. Cl.
*C12N 15/82* (2006.01)

(52) U.S. Cl.
CPC ..... *C12N 15/8273* (2013.01); *C12N 15/8222* (2013.01); *C12N 15/8266* (2013.01)

(58) Field of Classification Search
None
See application file for complete search history.

(56) References Cited

U.S. PATENT DOCUMENTS

| 5,689,042 A | 11/1997 | Amasino et al. |
| 2002/0016980 A1 | 2/2002 | Alberte et al. |

FOREIGN PATENT DOCUMENTS

| EP | 0 480 730 A2 | 4/1992 |
| WO | WO 96/17945 A1 | 6/1996 |
| WO | WO 96/29858 A1 | 10/1996 |
| WO | WO 99/29159 | * 6/1999 |
| WO | WO 99/29159 A1 | 6/1999 |
| WO | WO 02/20772 A1 | 3/2002 |
| WO | WO 03/050287 A2 | 6/2003 |
| WO | WO 03/087313 | * 10/2003 |
| WO | WO 2004/000007 A2 | 12/2003 |
| WO | WO 2004/076638 A2 | 9/2004 |

OTHER PUBLICATIONS

Kim et al. (Plant Molecular Biology, 24:105-117, 1994).*
Benfey et al. (Science 250:959-966, 1990).*
Donald et al. (EMBO J. 9:1717-1726, 1990).*
Wells (Biochemistry 29:8509-8517, 1990).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Ngo et al., (The Protein Folding Problem and Tertiary Structure Prediction, K. Merz., and S. Le Grand (eds.) pp. 492-495,1994).*
Synkova et al. (Physiologia Plantarum, 112(4):513-523, 2001).*
Clark et al. (J. Amer. Scoc. Hort.Sci. 129(1):93-99, Jan. 2004).*
Hajouj, T., et al., "Cloning and Characterization of a Receptor-Like Protein Kinase Gene Associated with Senescence," *Plant Physiology*, vol. 124, pp. 1305-1314 (Nov. 2000).
The Supplementary European Search report from EP 06739467.6 dated Oct. 18, 2008 (4 pages).
The European Search Report from EP 11155855.7 dated Apr. 11, 2011 (5 pages).
Boonman et al.; "Functional Signficance of Shade-Induced Leaf Senescence in Dense Canopies: An Experimental Test Using Transgenic Tobacco"• *The American Naturalist*; 168(5):597-607 (2006).
Cowan et al.; "Effects of senescence-induced alteration in cytokinin metabolism on source-sink relationships and ontogenic and stress-induced transitions in tobacco"; *Planta*; 221:801-814 (2005).
Dervinis et al. "Prevention of leaf senescence in petunia via genetic transformation with SAG-/IPT"; *Proc. Fla. State Hort. Soc.*; 111:12-15 (1998).
Gan et al.; "Inhibition of leaf senescence by autoregulated production of cytokinin"; *Science*; 270:(5244):1986-1988 (Dec. 1995).
McCabe et al.; "Effects of $P_{SAG12}$-IPT Gene Expression on Development and Senescence in Transgenic Lettuce"; *Plant Physiol.*; 127:505-516 (Oct. 2001).
Munné-Bosch et al.; "Die and let live: leaf senescence contributes to plant survival under drought stress"; *Funct. Plant Biol.*; 31:203-216 (2004).
Rivero et al.; "Cytokinin-Dependent Photorespiration and the Protection of Photosynthesis During Water Deficit"; *Plant Physiol.*; 150:1530-1540 (2009).
Rivero et al.; "Delayed leaf senescence induces extreme drought tolerance in a flowering plant"' *Proc. Natl. Acad. Sci.*; .104(49):19631-19636 (Dec. 2007) ePub Nov 28, 2007.
Smart et al.;"Delayed leaf senescence in tobacco plants transformed with TMR, a gene for cytokinin production in *Agrobacterium*"; *Plant Cell*; 3(7):647-656 (Jul. 1991).
Office Action mailed Nov. 1, 2016 in Brazilian Application No. PI0607732-3, 7 pages.
Blonstein et al., "A Cytokinin-Resistant Mutant of*Nicotiana plumbaginifolia* is Wilty," Planta, (1991) 183:244-250.
Itai, et al., "Cytokinin Activity in Water-Stressed Shoots," *Plant Physiol.* (1971) 47, 87-90.

* cited by examiner

*Primary Examiner* — Vinod Kumar
(74) *Attorney, Agent, or Firm* — Kilpatrick Townsend & Stockton LLP

(57) ABSTRACT

The present invention relates to the development of drought-resistant plants. This invention is directed to the preparation of transgenic plants that express a protein involved in cytokinin synthesis under the control of a senescence-inducible promoter. More specifically, this invention relates to the preparation of transgenic plants that express an isopentenyl transferase under the control of a senescence-associated receptor kinase (SARK) promoter.

10 Claims, 5 Drawing Sheets

FIG. 1
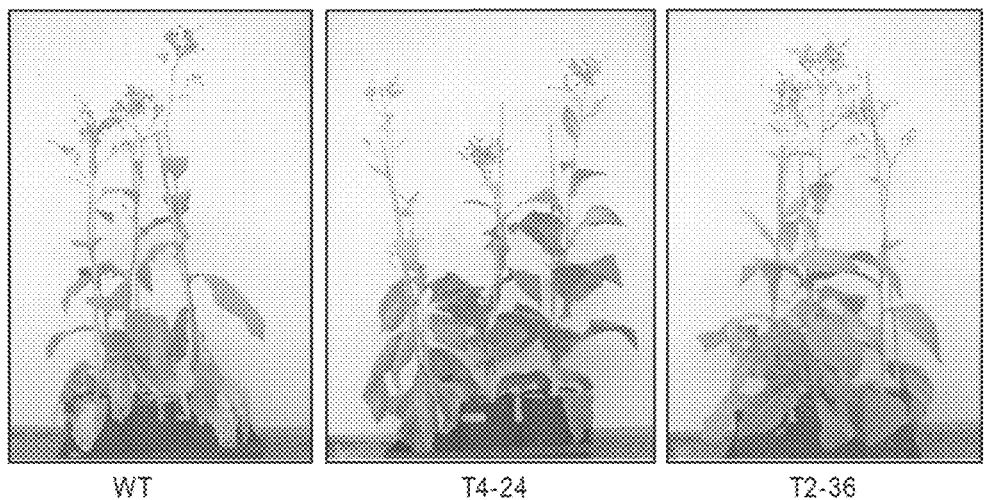
5 days dehydration
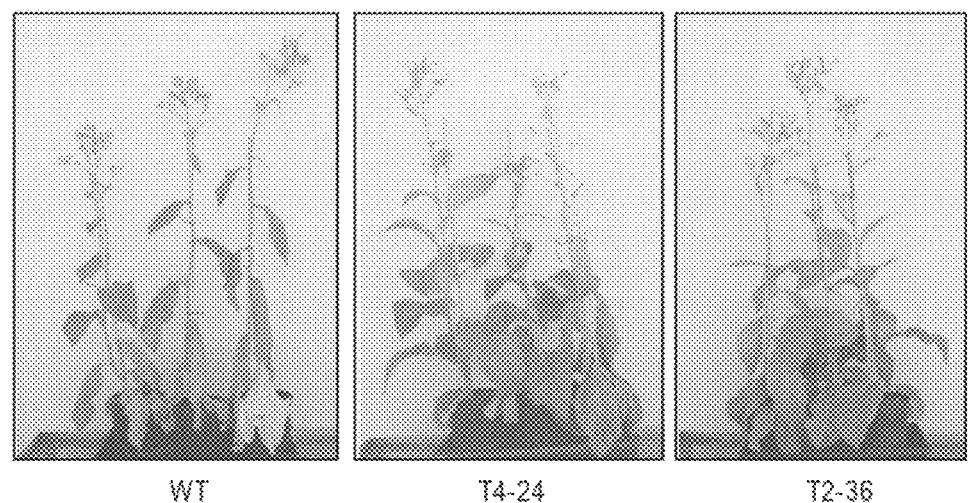
7 days dehydration

FIG. 1 (CONT.)
WT     T4-24     T2-36
16 days dehydration
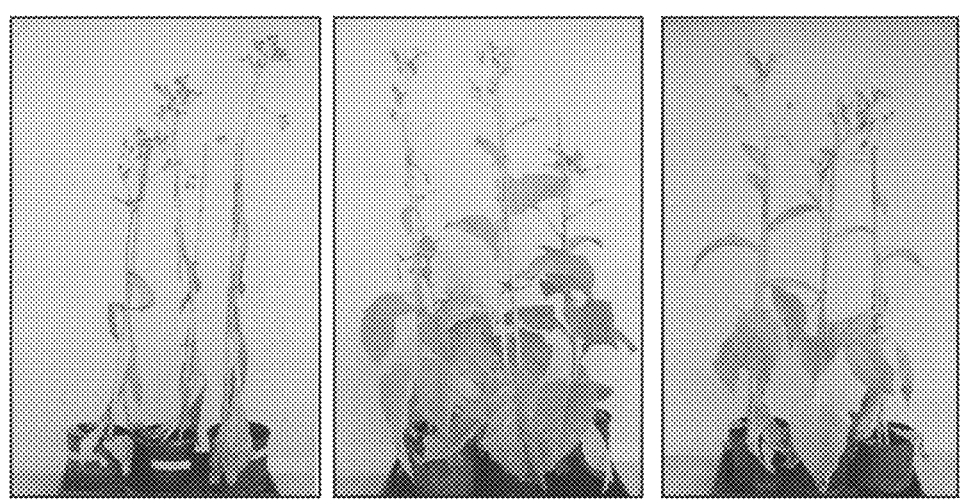
WT     T4-24     T2-36
8 days rehydration

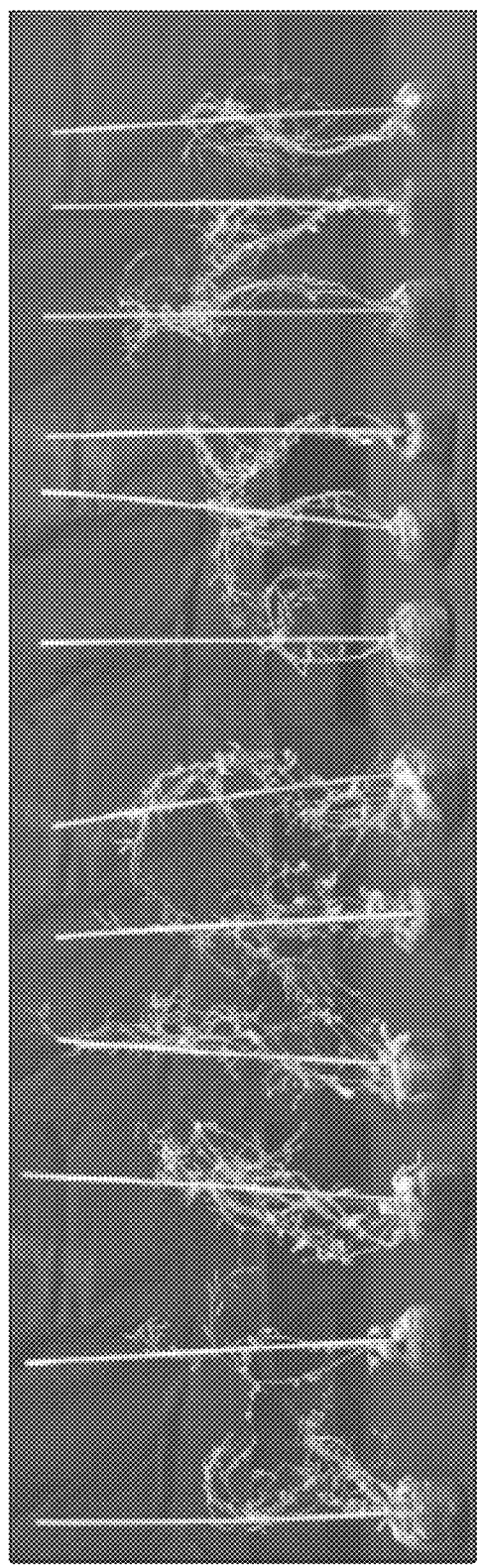

SEQUENCE LISTING

<160> NUMBER OF SEQ ID NOS: 9

<210> SEQ ID NO 1
<211> LENGTH: 1631
<212> TYPE: DNA
<213> ORGANISM: Phaseolus vulgaris
<220> FEATURE:
<223> OTHER INFORMATION: senescence-associated receptor like protein
      kinase (SARK) promoter, 5' region of SARK gene

<400> SEQUENCE: 1

```
ttcttcctta gatgctgtca caatcatttt cattattttt atatttggtt ttactgcaca       60
agtgacataa tgagtgctga attgtggtat tgtgggaacc ttaagcaata gtttcattag      120
accacttgtg caggttttg gggtggtaga aggaatgctc gttgtctctg aatgagttct      180 atttcatct ttagaaacta gtaatttagt tagttttggg tctcgtggtt ctacagaggg      240
ttgagatact tttgaagtat ctctctttta ttatattata cttttgctg ataaaaaaag      300 gtaggtagtt ttttttggaa tattttgtag gattttgtgg aggtgtttgg tataaggatt      360
gaaatatttc aaaaatattt ccatttaatt tacttttct tataaaaaaa atcctccatg      420
```

```
aaacaagatc atcttctaga acaacaagt aatatattag aatctctttc tgaattttct    480
catttgtgag ttatagtact ttttttccaa taataattat aagtggtaag atgtgtggtt    540
gtggaagttg aaggaaaga aggaaagaaa ggttagtttt tgttttgtat ttgaaagtaa    600
gtcaaggtca ttggcttagg gttctaccac tgcaactatt ccacattggc ttctaccact    660
gcaattattc cacattggct tgtactgtaa ggacaaacct tggcatgtca atacttttc    720 atcacatata accatattat aaactacttt ccatctccat tattcatcca ccaaaatcta    780
gagtcactga gagtgcagat aacacaattc tctaatataa aaatcagttt gtattcaata    840
tactgcaaaa aacttatgga cctgcatcta attttcggtc caacttgcac aggaaagacg    900
acgaccgcga tagctcttgc ccagcagaca gggcttccag tcctttcgct tgatcgggtc    960
caatgctgtc ctcaactatc aaccggaagc ggacgaccaa cagtggaaga actgaaagga   1020
acgacgcgtc tctaccttga tgatcggcct ctggtggagg gtatcatcgc agccaagcaa   1080
gctcatcata ggctgatcga ggaggtgtat aatcatgagg ccaacggcgg gcttattctt   1140
gagggaggat ccacctcgtt gctcaactgc atggcgcgaa acagctattg gagtgcagat   1200
tttcgttggc atattattcg ccacaagtta cccgaccaag agaccttcat gaaagcggcc   1260
aaggccagag ttaagcagat gttgcacccc gctgcaggcc attctattat tcaagagttg   1320
gtttatcttt ggaatgaacc tcggctgagg cccattctga agagatcga tggatatcga   1380 tatgccatgt tgtttgctag ccagaaccag atcacgcag atatgctatt gcagcttgac   1440
gcaaatatgg aaggtaagtt gattaatggg atcgctcagg agtatttcat ccatgcgcgc   1500
caacaggaac agaaattccc ccaagttaac gcagccgctt tcgacggatt cgaaggtcat   1560
ccgttcggaa tgtattaggt tacgccagcc ctgcgtcgca cctgtcttca tctggataag   1620
atgttcagat c                                                         1631

<210> SEQ ID NO 2
<211> LENGTH: 1919
<212> TYPE: DNA
<213> ORGANISM: Agrobacterium tumefaciens
<220> FEATURE:
<223> OTHER INFORMATION: isopenenyl transferase (IPT) from Ti plasmid
      Bo542
<220> FEATURE:
<221> NAME/KEY: CDS
<222> LOCATION: (690)..(1409)
<223> OTHER INFORMATION: IPT

<400> SEQUENCE: 2
ggatcccgtt acaagtattg cacgttttgt aaattgcata ttaatgcaat ctggatgttt     60 ataacgaat gtaatggcgt agaaatatgt attttattgt atttatcttt cactatgttg    120
aagtttgcaa taatatgcta atgtaaaatt aaaaaattat gtactgccgc atttgttcaa    180
atggcgccgt tatttcaaaa atatcttga ttttgttacg aggacaacga ctgcaggaag    240
taaataaaag acgctgttgt taagaaattg ctatcatatg tgcccagcta tagggccatt    300
taagttcaat tgtgaaatag ccgcccttat tttgacgtct catcaaatca aatattaaaa    360
aatatctcac tctgtcgcca gcaatgatgt aataaccgca gaaagtgag agtaaatcgc    420 ggaaaaacgt cgccgagtgg catgaatagc ggcctccgta ttgctgattt agtcagcttt    480
atttgactta agggtgccct cgttagtgac aaattgcttt caaggagaca gccatgcccc    540
acactttgtt gaaaaacaag ttgccttttg ggaagaacct aaagccactt gctcttcaag    600
gaggaatatc gaggaagaga ataatacagc ctctggtaca gacttctctt gtgcaaaaat    660
```

| | |
|---|---:|
| caatttgtat tcaacatatc gcaagaccg atg gat cta cgt cta att ttc ggt<br>                                                Met Asp Leu Arg Leu Ile Phe Gly<br>                                                    1                  5 | 713 |
| cca act tgc aca gga aag aca tcg act gcg ata gct ctt gcc cag cag<br>Pro Thr Cys Thr Gly Lys Thr Ser Thr Ala Ile Ala Leu Ala Gln Gln<br>      10                   15                   20 | 761 |
| act ggc ctc cca gtc ctc tcg ctc gat cgc gtc caa tgc tgt cct caa<br>Thr Gly Leu Pro Val Leu Ser Leu Asp Arg Val Gln Cys Cys Pro Gln<br> 25                  30                 35                 40 | 809 |
| cta tca acc gga agc ggg cga cca aca gtg gaa gaa ctg aaa gga acg<br>Leu Ser Thr Gly Ser Gly Arg Pro Thr Val Glu Glu Leu Lys Gly Thr<br>               45                 50                 55 | 857 |
| act cgt ctg tac ctt gat gat cgc cct ttg gta aag ggt atc att aca<br>Thr Arg Leu Tyr Leu Asp Asp Arg Pro Leu Val Lys Gly Ile Ile Thr<br>          60                 65                 70 | 905 |
| gcc aag caa gct cat gaa cgg ctc att gcg gag gtg cac aat cac gag<br>Ala Lys Gln Ala His Glu Arg Leu Ile Ala Glu Val His Asn His Glu<br> 75                  80                 85 | 953 |
| gcc aaa ggc ggg ctt att ctt gag gga gga tct atc tcg ttg ctc agg<br>Ala Lys Gly Gly Leu Ile Leu Glu Gly Gly Ser Ile Ser Leu Leu Arg<br>      90                 95                100 | 1001 |
| tgc atg gcg caa agt cgt tat tgg aac gcg gat ttt cgt tgg cat att<br>Cys Met Ala Gln Ser Arg Tyr Trp Asn Ala Asp Phe Arg Trp His Ile<br>105                 110                115                120 | 1049 |
| att cgc aac gag tta gca gac gag gag agc ttc atg agc gtg gcc aag<br>Ile Arg Asn Glu Leu Ala Asp Glu Glu Ser Phe Met Ser Val Ala Lys<br>               125                130                135 | 1097 |
| acc aga gtt aag cag atg tta cgc ccc tct gca ggt ctt tct att atc<br>Thr Arg Val Lys Gln Met Leu Arg Pro Ser Ala Gly Leu Ser Ile Ile<br>          140                145                150 | 1145 |
| caa gag ttg gtt caa ctt tgg agg gag cct cgg ctg agg ccc ata ctg<br>Gln Glu Leu Val Gln Leu Trp Arg Glu Pro Arg Leu Arg Pro Ile Leu<br>155                 160                165 | 1193 |
| gaa ggg atc gat gga tat cga tat gcc ctg cta ttt gct acc cag aac<br>Glu Gly Ile Asp Gly Tyr Arg Tyr Ala Leu Leu Phe Ala Thr Gln Asn<br>       170                175                180 | 1241 |
| cag atc acg ccc gat atg cta ttg cag ctc gac gca gat atg gag aat<br>Gln Ile Thr Pro Asp Met Leu Leu Gln Leu Asp Ala Asp Met Glu Asn<br>185                 190                195                200 | 1289 |
| aaa ttg att cac ggt atc gct cag gag ttt cta atc cat gcg cgt cga<br>Lys Leu Ile His Gly Ile Ala Gln Glu Phe Leu Ile His Ala Arg Arg<br>               205                210                215 | 1337 |
| cag gaa cag aaa ttc cct ttg gtg ggc gcg aca gct gtc gaa gcg ttt<br>Gln Glu Gln Lys Phe Pro Leu Val Gly Ala Thr Ala Val Glu Ala Phe<br>          220                225                230 | 1385 |
| gaa gga cca cca ttt cga atg tga tagattgcac cagttttgtt tcagacttgt<br>Glu Gly Pro Pro Phe Arg Met<br>       235                240 | 1439 |
| cgctatttga ataagatgtt cgttctttgt tgtgttggtg tgttgtgata gaggcaagtg | 1499 |
| gtttgaaact tgttttact ggtttatttt cagtctcttg gacgatgttt tacaaatata | 1559 |
| atattgtgaa aattgtggtt ttatattcgt agaacgaaat aaatggtaag tatagccgtt | 1619 |
| atcaaaattt agcaaaaatt gttaaaggtt cttttatgcg gtgaggttgt cgacttttca | 1679 |
| tcattgtcgc gtaaggagtt acggatatcc ataactgtaa aaacgccgca gaatttacgg | 1739 |
| gtggtgcatt tagtttgccg ttcaacatga ttttggcaat agttggtaac caagcactag | 1799 |
| ccaaccgttc gataatcact taatcgatgg aaccgttcag ctttccttcg tgaggctgct | 1859 |
| cttgatgatg agctgccgtc tagtttttat aacgccgggt tacgcattat agacaagctt | 1919 |

```
<210> SEQ ID NO 3
<211> LENGTH: 239
<212> TYPE: PRT
<213> ORGANISM: Agrobacterium tumefaciens
<220> FEATURE:
<223> OTHER INFORMATION: isopenenyl transferase (IPT) from Ti plasmid
      Bo542

<400> SEQUENCE: 3

Met Asp Leu Arg Leu Ile Phe Gly Pro Thr Cys Thr Gly Lys Thr Ser
 1               5                  10                  15

Thr Ala Ile Ala Leu Ala Gln Gln Thr Gly Leu Pro Val Leu Ser Leu
                20                  25                  30

Asp Arg Val Gln Cys Cys Pro Gln Leu Ser Thr Gly Ser Gly Arg Pro
            35                  40                  45

Thr Val Glu Glu Leu Lys Gly Thr Thr Arg Leu Tyr Leu Asp Asp Arg
        50                  55                  60

Pro Leu Val Lys Gly Ile Ile Thr Ala Lys Gln Ala His Glu Arg Leu
 65                  70                  75                  80

Ile Ala Glu Val His Asn His Glu Ala Lys Gly Gly Leu Ile Leu Glu
                85                  90                  95

Gly Gly Ser Ile Ser Leu Leu Arg Cys Met Ala Gln Ser Arg Tyr Trp
            100                 105                 110

Asn Ala Asp Phe Arg Trp His Ile Ile Arg Asn Glu Leu Ala Asp Glu
        115                 120                 125

Glu Ser Phe Met Ser Val Ala Lys Thr Arg Val Lys Gln Met Leu Arg
130                 135                 140

Pro Ser Ala Gly Leu Ser Ile Ile Gln Glu Leu Val Gln Leu Trp Arg
145                 150                 155                 160

Glu Pro Arg Leu Arg Pro Ile Leu Glu Gly Ile Asp Gly Tyr Arg Tyr
                165                 170                 175

Ala Leu Leu Phe Ala Thr Gln Asn Gln Ile Thr Pro Asp Met Leu Leu
            180                 185                 190

Gln Leu Asp Ala Asp Met Glu Asn Lys Leu Ile His Gly Ile Ala Gln
        195                 200                 205

Glu Phe Leu Ile His Ala Arg Arg Gln Glu Gln Lys Phe Pro Leu Val
    210                 215                 220

Gly Ala Thr Ala Val Glu Ala Phe Glu Gly Pro Pro Phe Arg Met
225                 230                 235

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:inverse PCR
      primer 1 to isolate upstream region of 5' end of
      SARK gene

<400> SEQUENCE: 4
acgtccaacc aaagacc                                                    17

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:inverse PCR
      primer 2 to isolate upstream region of 5' end of SARK gene,
      thermal asymmetric interlaced (TAIL) PCR primer 1 to isolate
      fragment upstream of 5' region of SARK gene
```

```
<400> SEQUENCE: 5
tctgcagcta gtgcgatatc c                                            21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:thermal
      asymmetric interlaced (TAIL) PCR primer 2 to
      isolate fragment upstream of 5' region of SARK
      gene

<400> SEQUENCE: 6
ttggtggatg aataatggag                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:thermal
      asymmetric interlaced (TAIL) PCR primer 3 to
      isolate fragment upstream of 5' region of SARK
      gene

<400> SEQUENCE: 7
actgtaactc acaaattaga                                              20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:primer
      SARKIPF for PCR amplification of pSARK:IPT

<400> SEQUENCE: 8
ttccttagat gctgtcacaa tca                                          23

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:primer
      SARKIPTR for PCR amplification of pSARK:IPT

<400> SEQUENCE: 9
gaacatctta tccagatgaa gacag                                        25
```

DROUGHT-RESISTANT PLANTS

CROSS-REFERENCES TO RELATED APPLICATIONS

This application is a U.S. National Stage Application of PCT/US2006/010678, filed Mar. 21, 2006, which claims the benefit of U.S. Provisional Application No. 60/664,035, filed Mar. 21, 2005, all of which are hereby incorporated by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Physiological and genetic studies indicate that senescence is a highly regulated process (Nooden, Senescence and Aging in Plants, (L. D. Nooden and A. C. Leopold, Ed.), pp. 391-439, Academic Press, San Diego, Calif., 1988; Thomas, et al., Ann. Rev. Plant Physiol. 31:83-111, 1980). Molecular studies suggest that changes in gene expression are associated with the senescence program. For example, the level of mRNA encoding proteins involved in photosynthesis decrease during senescence (Bate, et al., J. Exp. Bot. 42:801-811, 1991; Hensel, et al., Plant Cell 5:553-564, 1993; Jiang, et al., Plant Physiol. 101:105-112, 1993), while mRNA levels of genes encoding proteins thought to be involved in the senescence program increase (Graham, et al., Plant Cell 4:349-357, 1992, Hensel, et al., Plant Cell 5:553-564, 1993; Kamachi, et al., Plant Physiol. 93:1323-1329, 1992; Taylor, et al., Proc. Natl. Acad. Sci. USA 90:5118-5122, 1993).

It has been suggested that senescence specific promoters can be used to drive the expression of select genes during senescence. U.S. Pat. No. 5,689,042, for example, utilizes a genetic construct comprising a senescence specific promoter, SAG12, operably linked to a *Agrobacterium* isopentyl transferase (IPT)-coding DNA sequence not natively connected to the promoter sequence. Transgenic plants comprising this construct retain green leaves longer by driving the expression of IPT by means of the SAG12 promoter. IPT is known to increase the level of cytokinin, a class of plant hormones the concentration of which declines during senescence and thus may play a role in controlling leaf senescence.

Similarly, Gan and Amasino show that inhibition of leaf senescence can be achieved by autoregulated production of cytokinin (Gao, et al., Science 270:1986-1988, 1995). Other senescence-inducible promoters have been identified. For example, the SARK promoter from *Phaseolus vulgaris* is described in WO 99/29159 and Hajouj et al. *Plant Physiol.* 124:1305-1314 (2000).

A useful and desirable aspect of internally regulating the expression of the gene of interest is in the ability to regulate the expression only in those cells undergoing senescence thus leaving normal cells unaffected and spared from the possibly negative effects of cytokinin overproduction.

Although the use of SAG12 controlled expression of IPT has been shown to control leaf senescence, other phenotypes of such plants are not well understood. The present invention addresses these and other needs.

BRIEF SUMMARY OF THE INVENTION

The present invention relates to the development of drought-resistant plants. The methods of the invention provide plants with increased drought-resistance and other advantageous characteristics, such as increased yield. In addition, the plants of the invention also have greater water-use efficiency. This invention is directed to the preparation of transgenic plants that express a protein involved in cytokinin synthesis under the control of a senescence-inducible promoter.

The methods of the invention comprise (a) introducing into a population of plants a recombinant expression cassette comprising a SARK promoter operably linked to a nucleic acid sequence encoding a protein involved in cytokinin synthesis; and (b) selecting a plant that is resistant to drought stress. The step of introducing the expression cassette can be carried out using any known method. For example, the expression cassette can be introduced by a sexual cross or using *Agrobacterium*.

The SARK promoter is conveniently prepared from *Phaseolus vulgaris* and may have a sequence at least 95% identical to the SARK promoter sequence of SEQ ID NO: 1. In some embodiments, the protein involved in cytokinin synthesis is isopentenyl transferase (IPT) from *Agrobacterium*. An exemplary sequence (IPT) sequence is one that is at least 95% identical to the protein encoded by SEQ ID NO: 1 or to SEQ ID NO: 3.

The sequence can be introduced into any plant capable of transformation with recombinant expression constructs. The expression in tobacco is exemplified herein. Other plants conveniently used in the invention include turf grasses.

BRIEF DESCRIPTION OF THE DRAWINGS

FIG. 1 shows that WT tobacco plants displayed a progressing leaf wilting, whereas two independent transgenic lines, T4-24 and T2-36, did not show wilting symptoms during a drought stress of 5 and 7 days without water. A period of 16 days dehydration caused severe irreversible wilting of the WT plants and less severe, and reversible wilting in T4-24 and T2-36 plants. Rehydration (8 days rehydration) caused recovery of T4-24 and T2-36 plants, whereas the WT plants could not be recovered from the drought stress.

FIG. 4 shows WT *Arabisdopsis* plants and T1 transgenic plants (pSARK:IPT) after drought stress and 5 days of rehydration.

DETAILED DESCRIPTION OF THE INVENTION

Definitions

Figure 2:
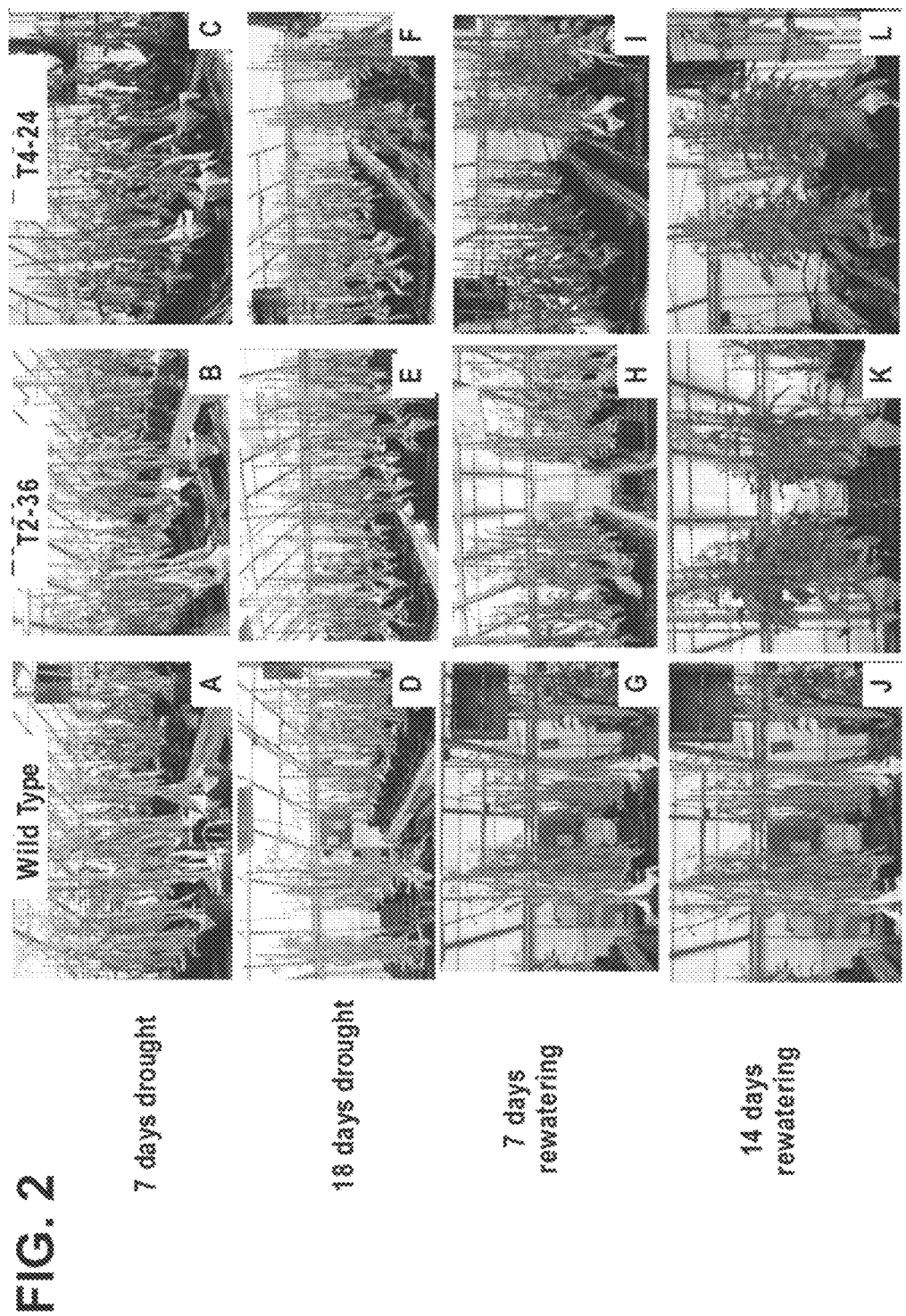
FIGS. 2A-2L show 4 month-old tobacco plants subjected to drought stress followed by rehydration. Both wild type (FIG. 2A) and transgenic plants (FIGS. 2B and 2C) displayed leaf wilting symptoms after 7 days of drought. The leaf wilting symptoms became more pronounced after 18 days of drought, both in WT (FIG. 2D) and the two transgenic lines (FIGS. 2E and 2F). Rehydration of the plants for 7 days had little effect on wilted WT plants (FIG. 2G), but induced partial recovery of the transgenic lines (FIGS. 2H and 2I) with transgenic line T4-24 (FIG. 2I) showing better recovery than transgenic line T2-36 (FIG. 2H). Rehydration of the plants for 14 days did not recovered WT plants (FIG. 2J), but fully recovered both transgenic lines (FIGS. 2K and 2L).

As used herein, the terms "drought-resistance" or "drought-tolerance" refer to the ability of a plant to recover from periods of drought stress (i.e., little or no water for a period of days). Typically, the drought stress will be at least 5 days and can be as long as 18 to 20 days.

The term "water-use efficiency" refers to the ability of a plant to grow with substantially no yield penalty under extended periods with less than normal (typically about half) amounts of water.

The term "senescence" (also referred to as programmed cell death) refers to a genetically controlled, active process by which plant cells and tissues loose organization and function.

The term "senescence associated gene" refers to a gene involved in senescence. The expression of such a gene may be induced (or altered) during the process of senescence.

As used herein, the term "promoter" includes all sequences capable of driving transcription of a coding sequence in a plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

A "maturation-inducible promoter" is a promoter that confers temporal specificity of an operably linked coding sequence such that expression occurs at the completion of maturation and/or during the process of senescence.

A "senescence-inducible promoter" is a promoter that confers temporal specificity of an operably linked coding sequence such that expression occurs during the process of senescence.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

Two nucleic acid sequences or polypeptides are said to be "identical" if the sequence of nucleotides or amino acid residues, respectively, in the two sequences is the same when aligned for maximum correspondence as described below.

The term "complementary to" is used herein to mean that the sequence is complementary to all or a portion of a reference polynucleotide sequence.

Optimal alignment of sequences for comparison may be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, at least 80% sequence identity, at least 85%, 90%, 93% 95%, or 97% compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, 60%, 70%, 80%, 90%, 95% or 97% compared to a reference sequence using the programs described herein. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

For the purposes of this disclosure, stringent conditions for hybridizations are those which include at least one wash in 0.2×SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions.

The term "expression cassette" refers to any recombinant expression system for the purpose of expressing a nucleic acid sequence of the invention in vitro or in vivo, constitutively or inducibly, in any cell, including, in addition to plant cells, prokaryotic, yeast, fungal, insect or mammalian cells. The term includes linear or circular expression systems. The term includes all vectors. The cassettes can remain episomal or integrate into the host cell genome. The expression cassettes can have the ability to self-replicate or not, i.e., drive only transient expression in a cell. The term includes recombinant expression cassettes which contain only the minimum elements needed for transcription of the recombinant nucleic acid.

Preparation of Expression Cassettes

The expression cassettes of the invention comprise senescence inducible promoters. The SARK promoter from *Phaseolus vulgaris* is exemplified below. The promoter is described in WO 99/29159 and Hajouj et al. *Plant Physiol.* 124:1305-1314 (2000). Other suitable promoters include the *Arabidoposis* SAG12 promoter as described in Gan et al., *Science*, 270:1986-8 (1995). One skill will recognize that the particular promoter used in the constructs of the invention, so long as expression is induced by senescence. Thus, for example, promoters form homologues of the SARK or SAG12 genes from other species can be conveniently used in the expression cassettes of the invention.

The promoters are used to drive expression of gene encoding a protein that inhibits or slows the senescence process. In some preferred embodiments, the gene encodes a protein involved in cytokinin synthesis. For example, isopentenyl transferase (IPT) catalyzes the synthesis of cytokinin. Examples of IPT sequences are presented in: Crespi et al., *EMBO J.* 11:795-804 (1992); Goldberg et al., *Nucleic Acids. Res.* 12:4665-4677 (1984); Heide Kamp et al., *Nucleic Acids Res.*, 11:6211-6223 (1983); Strabala et al., *Mol. Gen. Genet.* 216:388-394 (1989) GenBank Accession Number: NC_003308, as well as X14410 (see SEQ ID NOs: 2 and 3)

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717-2722 (1984). Electroporation techniques are described in Fromm et al *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillian Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes of the invention can be used to confer drought resistance on essentially any plant. Thus, the invention has use over a broad range of plants, including species from the genera *Asparagus, Atropa, Aveiza, Brassica, Citrus, Citrullus, Capsicum, Cucuinis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Paniieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*.

In some embodiments, the methods of the invention are used to confer drought resistance on turf grasses. A number of turf grasses are known to those of skill in the art. For example, fescue, *Festuca* spp. (e.g., *F. arundinacea, F. rubra, F. ovina* var. *iduriuscula*, and *F. ovina*) can be used. Other grasses include Kentucky bluegrass *Poa pratensis* and creeping bentgrass *Agrostis palustris*.

Those of skill will recognize that a number of plant species can be used as models to predict the phenotypic effects of transgene expression in other plants. For example, it is well recognized that both tobacco (*Nicotiania*) and *Arabidopsis* plants are useful models of transgene expression, particularly in other dicots.

Drought resistance can assayed according to any of a number of well-know techniques. For example, plants can be grown under conditions in which less than optimum water is provided to the plant. Drought resistance can be determined by any of a number of standard measures including turgor pressure, growth, yield and the like. In some embodiments, the methods described in the Example section, below can be conveniently used.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Identification of the SARK (Senescence-Associated Receptor Kinase) Gene

The cDNA of the SARK gene was isolated from *Phaseolus vulgaris* by a differential display technique as described in Hajouj et al. (2000). The sequence of the full length cDNA of SARK revealed that it encodes a serine/threonine protein kinase. A hydrophobic transmembrane domain was observed suggesting that the SARK gene encodes a receptor kinase (Hajouj et al. 2000). Northern blot analysis revealed the up-regulation of the SARK gene during early stages of leaf senescence. The initiation of the SARK gene expression preceded any visual sign (yellowing) of the attached bean leaf senescence. Leaf discs, when incubated in the dark, displayed accelerated yellowing.

Similar to the intact attached leaves, transcripts levels of the SARK gene increased at the onset of the senescence process prior to any visual yellowing of the leaf (Hajouj et al (2000)). Thus, we can define the SARK gene as a senescence-associated gene (SAG). Moreover, the appearance of the SARK transcripts at the very early stages of senescence both in the attached or detached leaves suggests a regulatory role in the senescence process. Antibodies raised against the SARK protein were produced and used for western blot analysis. The temporal pattern of the levels of the SARK protein resembled that of the RNA and further support the notion that the SARK protein is associated with the senescence processes of detached and attached leaves.

Isolation of the SARK Promoter

The upstream region of 5'-end of the SARK gene was isolated by the inverse PCR approach as described by Maniatis et al. (Molecular cloning, a laboratory manual 2$^{nd}$ edition. Bean genomic DNA was isolated by plant DNA extraction kit (Scotlab) according the manufacturer's instructions. The DNA was digested with the restriction enzyme XbaI and recirculated by relegation. The following primers were used for the PCR reaction.

```
                                          (SEQ ID NO: 4)
    1)      5' ACGTCCAACCAAAGACC 3'

(SEQ ID NO: 5)
    2)      5' TCTGCAGCTAGTGCGATATCC 3'
```

The PCR reaction was performed under the following conditions: 30 sec at 94° C., 30 sec at 55° C., 2 min at 72° C. for 40 cycles and then 10 min at 720 C.

A DNA fragment of 1.4 kb was amplified. DNA sequencing of this fragment revealed that it included 340 bp of the 5' end of the SARK DNA. This sequence revealed the existence of an intron close to the 5' end of the SARK gene.

To isolate a longer fragment upstream of the 5' region of the SARK gene, a thermal asymmetric interlaced (TAIL) PCR technique was performed as described by Liu et al. (Plant J. 8: 457-463). Three PCR primers were used:

```
                                          (SEQ ID NO: 5)
    1)      5' TCTGCAGCTAGTGCGATATCC 3'

(SEQ ID NO: 6)
    2)      5' TTGGTGGATGAATAATGGAG 3'

(SEQ ID NO: 7)
    3)      5' ACTGTAACTCACAAATTAGA 3'
```

Three PCR reactions were carried out to amplify target sequences.

The PCR products were sequenced. Approximately 800 bp of the 5' end of the cDNA were identified and are shown in SEQ ID NO: 1. The PCR fragment was cloned in pUC57. Creation of Transgenic Plants Carrying the pSARK:IPT Construct.

The *Agrobacterium* ipt (isopentenyl transferase), the enzyme that catalyzes the rate limiting step in cytokinins biosynthesis was fused to the SARK promoter. Gan and Amasino (Science 270; 1996 (1995) have shown that the promoter of the *Arabidopsis* SAG12 gene (senescence-associated gene) when linked to the ipt gene induced the synthesis of cytokinins and delayed the process of leaf senescence. The *Agrobacterium* IPT was operably linked to the 830 nucleotide length promoter of the SARK gene and introduced as a HinII/XbaI fragment into pBI101 (ClonTech) to create the pBI p-SARK:IPT. *Agrobacterium* transformation was performed by electroporation.

Tobacco Transformation

Plants were transformed via the *Agrobacterium*-mediated transformation method. Expression of *Agrobacterium* Isopentyl Transferase (IPT) gene under the regulation of the SARK promoter caused delayed senescence of the tobacco leaves. The transgenic tobacco containing the p-SARK-IPT has shown considerable delay in the regular senescence of both the individual leaves and the whole plants. The WT plants flower usually 3 to 3.5 months after germination and start to exhibit yellowing of the first leaves (at the bottom) after 4 months. However, the transgenic plants displayed a significant delayed senescence and did not show any yellowing of the first leaves until 10 months after germination.

Detached leaves of the transgenic tobacco showed also a significant delay in yellowing when incubated under dark conditions. Normally, detached tobacco leaves display initial yellowing after 5-6 days of incubation in the dark and complete their yellowing after 10-12 days. The detached leaves of the transgenic plants, however, did not show any sign of yellowing for 20 days and even after 30 days of dark incubation they were still green although initial yellowing was observed. These results demonstrated that in addition to the attached leaves, the autoregulatory mechanism of cytokinins synthesis in detached leaves of the transgenic plants was also functional.

*Arabidopsis* Transformation

PCR amplification of the pSARK:IPT using the following primers was performed with the by the Pfu turbo DNA polymerase (Stratagene).

```
SARKIPF
                                          (SEQ ID NO: 8)
5'T T C C T T A G A T G C T G T C A C A A T C A 3'

SARKIPTR
                                          (SEQ ID NO: 9)
5'G A A C A T C T T A T C C A G A T G A A G A C A
G 3'
```

The template for the PCR amplification was the transgenic tobacco DNA containing the pSARK:IPT The PCR product (PSARK:IPT) was cloned with the TOPO cloning kit into Topo competent cells (DH5α-T1) according to the instruction of the manufacturer (Invitrogen).

DNA plasmid minipreps was performed with the Qiaprep kit (Qiagen).

The plasmid was digested with BglII and EcoRI and was ligated with the Cambia 1380 vector (CAMBIA, Canberra Australia)

Electroporation of the Cambia vector carrying the pSARK:IPT was performed into (DH5α) competent cells. DNA plasmid miniprep of the transfected DH5α colonies was carried out with the Qiaprep kit (Qiagen). The Cambia vector containing the pSARK:IPT was electrophoretically introduced into *Agrobacterium* for plant transformation. *Arabidopsis thaliana* plants were transformed by the vacuum infiltration technique with *Agrobacterium tumefaciens* containing the pSARK:IPT and the hygromycin resistance gene (hptIIgene) for selection in plants.

Expression of Isopentyl Transferase (IPT) Under the Regulation of SARK Gene Promoter in Tobacco Plants Confers Drought Resistance.

Transgenic tobacco plants carrying the pSARK:IPT have been grown in the greenhouse for 2-3 months. No morphological differences could be visualized between the transgenic and the WT plants during the first 3-4 months.

Following the initiation of flowering, 3 month old tobacco plants were subjected to drought stress (no water was added to the pots) for 5-16 days. The WT plants displayed a progressing leaf wilting (FIG. 1). However, the transgenic plants (two independent lines) did not show wilting symptoms (FIG. 1) during a drought stress of 5 and 7 days without water. Long dehydration periods of 16 days caused severe irreversible wilting of the WT plants and less severe, and reversible wilting in plants carrying the pSARK:IPT. Rehydration (re-watering of the dehydrated plants) caused recovery of the transgenic pSARK:IPT plants, whereas the WT plants could not be recovered (FIG. 1) from the drought stress.

Figure 3:
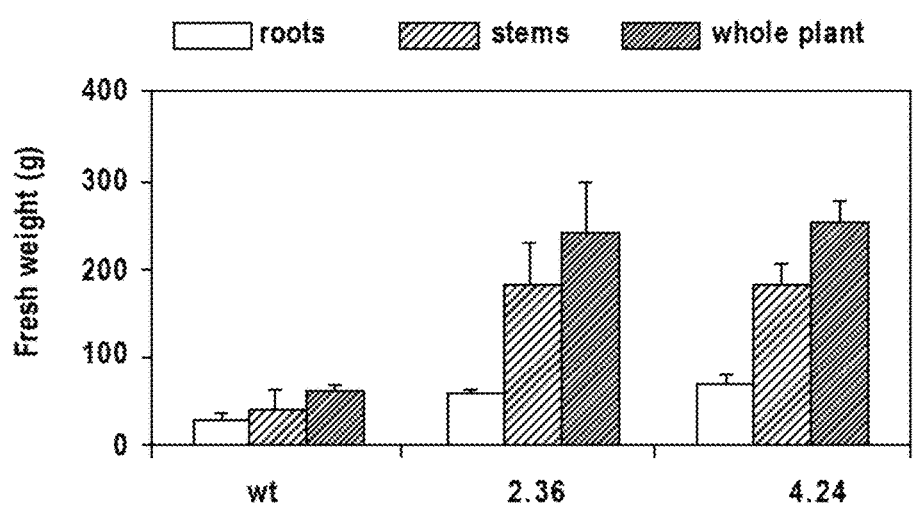
FIG. 3 Shows fresh weight of plants shown in FIG. 2 after 14-day rewatering. Values are Mean±SD (n=40).

Wild type plants (WT) and two transgenic lines of tobacco plants carrying the pSARK-IPT (T2-36 and T4-24) were grown in the greenhouse for 5 months. No morphological differences could be observed between the transgenic and the wild-type plants during the first 3-4 months of growth under optimal conditions. Following the initiation of flowering, 4 month-old tobacco plants were subjected to drought stress (no water was added to the pots) for a period of 18 consecutive days (FIG. 2, A-F). Both wild type (FIG. 2A) and transgenic plants (FIGS. 2B and 2C) displayed leaf wilting symptoms after 7 days of drought. The leaf wilting symptoms became more pronounced after 18 days of drought, both in WT (FIG. 2D) and the two transgenic lines (FIGS. 2E and 2F). Rehydration of the plants for 7 days had little effect on wilted WT plants (FIG. 2G), but induced partial recovery of the transgenic lines (FIGS. 2H and 2I) with transgenic line T4-24 (FIG. 2I) showing better recovery than transgenic line T2-36 (FIG. 2H). Rehydration of the plants for 14 days did not recovered WT plants (FIG. 2J), but fully recovered both transgenic lines (FIGS. 2K and 2L). Measurements of the Fresh Weight of the wild-type and transgenic plants at the end of the rehydration period showed that the transgenic lines attained a fresh weight of ~250 gram/plant, while the wild-type remained dry with a weight that did not exceed 20% of that of the transgenic lines (FIG. 2). FIG. 3 shows the fresh weight of plants shown in FIG. 2 after 14-day rewatering. Values are Mean±SD (n=40).

Expression of the IPT Gene Under the Regulation of the SARK Gene Promoter Confers Drought Resistance to Transgenic *Arabidopsis* Plants.

*Arabidopsis thaliana* plants were grown under long day's regime (16/8 h) at 23° C. No morphological and developmental differences could be distinguished between the WT and the transgenic (pSARK:IPT) plants grown under normal conditions. However, when two month-old plants (at the stage of advanced flowering) were subjected to drought stress (no water was added to the pots) they displayed differential stress resistance. The WT plants underwent severe irreversible wilting and leaf yellowing after 12 days of dehydration, whereas 10 different independent lines of the T1 transgenic plants (pSARK:IPT) showed mild wilting and recovered from the drought stress after 5 days of rehydration (FIG. 4).

What is claimed is:

1. A method of preparing a transgenic plant resistant to drought stress, the method comprising:
    (a) transforming a population of plants with a recombinant expression cassette comprising a senescence-associated receptor kinase (SARK) promoter from *Phaseolus vulgaris* operably linked to a nucleic acid sequence encoding a protein involved in cytokinin synthesis; and
    (b) selecting a transgenic plant that comprises the recombinant expression cassette and is resistant to drought stress, wherein the drought stress causes severe irreversible wilting in a plant that lacks the recombinant expression cassette.

2. The method of claim 1, wherein the step of transforming is carried out using *Agrobacterium*.

3. The method of claim 2, wherein the SARK promoter specifically hybridizes to the SARK promoter of SEQ ID NO: 1 under stringent conditions that include at least one wash in 0.2×SSC at 63° C. for 20 minutes.

4. The method of claim 1, wherein the protein involved in cytokinin synthesis is isopentenyl transferase.

5. The method of claim 4, wherein the nucleic acid sequence encoding the isopentenyl transferase is from *Agrobacterium*.

6. The method of claim 5, wherein the isopentenyl transferase is at least 95% identical to the protein encoded by SEQ ID NO: 1 or to SEQ ID NO: 3.

7. The method of claim 1, wherein the plant is a dicot.
8. The method of claim 7, wherein the plant is tobacco.
9. The method of claim 1, wherein the plant is a monocot.
10. The method of claim 9, wherein the plant is *Oryza*.

* * * * *